US011380029B2

(12) United States Patent
Markovitz

(10) Patent No.: US 11,380,029 B2
(45) Date of Patent: Jul. 5, 2022

(54) SYSTEM AND METHOD FOR MAPPING LOCAL ACTIVATION TIMES

(71) Applicant: St. Jude Medical, Cardiology Division, Inc., St. Paul, MN (US)

(72) Inventor: Craig Markovitz, Mahtomedi, MN (US)

(73) Assignee: ST. JUDE MEDICAL, CARDIOLOGY DIVISION, INC., St. Paul, MN (US)

( * ) Notice: Subject to any disclaimer, the term of this patent is extended or adjusted under 35 U.S.C. 154(b) by 371 days.

(21) Appl. No.: 16/494,519

(22) PCT Filed: May 2, 2018

(86) PCT No.: PCT/US2018/030687
§ 371 (c)(1),
(2) Date: Sep. 16, 2019

(87) PCT Pub. No.: WO2018/212996
PCT Pub. Date: Nov. 22, 2018

(65) Prior Publication Data
US 2020/0085329 A1  Mar. 19, 2020

Related U.S. Application Data

(60) Provisional application No. 62/507,289, filed on May 17, 2017.

(51) Int. Cl.
*G06T 11/20* (2006.01)
*G06T 5/00* (2006.01)
*A61B 5/339* (2021.01)

(52) U.S. Cl.
CPC ............ *G06T 11/206* (2013.01); *G06T 5/007* (2013.01); *A61B 5/339* (2021.01); *G06T 2210/41* (2013.01)

(58) Field of Classification Search
CPC ....... A61B 5/339; A61B 5/5349; A61B 5/283; G06T 11/206; G06T 2210/41; G16H 30/40
See application file for complete search history.

(56) References Cited

U.S. PATENT DOCUMENTS

| 5,697,377 A | 12/1997 | Wittkampf |
| 5,983,126 A | 11/1999 | Wittkampf |

(Continued)

FOREIGN PATENT DOCUMENTS

| WO | 2007/146864 | 12/2007 |
| WO | 2016/061387 A1 | 4/2016 |

OTHER PUBLICATIONS

International Search Report and Written Opinion for PCT Application No. PCT/US2018/030687, dated Aug. 8, 2018.

(Continued)

*Primary Examiner* — Michelle L Sams
(74) *Attorney, Agent, or Firm* — Wiley Rein LLP

(57) ABSTRACT

Local activation times (LATs) are mapped by computing an LAT range for a plurality of electrophysiology data points, splitting the LAT range into two or more LAT sub-ranges, splitting the LAT map into a corresponding number of LAT sub-maps, and associating a mapping sub-convention (e.g., a color spectrum, grayscale, and/or pattern density range) with each of the LAT sub-maps. The mapping sub-conventions can be scaled (e.g., linearly, logarithmically) to their respective LAT sub-ranges, allowing for an overall LAT map that offers increased granularity over LAT sub-ranges of particular interest to the practitioner. The LAT sub-maps can be updated in real time as additional electrophysiology data points are collected.

19 Claims, 4 Drawing Sheets

(56) References Cited

U.S. PATENT DOCUMENTS

| | | | |
|---|---|---|---|
| 6,256,628 B1 * | 7/2001 | Dobson | G06F 3/0481 |
| | | | 706/62 |
| 6,301,496 B1 | 10/2001 | Reisfeld | |
| 6,640,119 B1 | 10/2003 | Budd et al. | |
| 6,728,562 B1 | 4/2004 | Budd et al. | |
| 6,939,309 B1 | 9/2005 | Beatty et al. | |
| 6,947,785 B1 | 9/2005 | Beatty et al. | |
| 6,978,168 B2 | 12/2005 | Beatty et al. | |
| 6,990,370 B1 | 1/2006 | Beatty et al. | |
| 7,263,397 B2 | 8/2007 | Hauck et al. | |
| 7,885,707 B2 | 2/2011 | Hauck | |
| 9,675,266 B2 | 6/2017 | Afonso et al. | |
| 10,105,074 B2 | 10/2018 | Severino | |
| 2006/0020205 A1 * | 1/2006 | Kamiyama | A61B 8/469 |
| | | | 600/437 |
| 2012/0007868 A1 * | 1/2012 | Buck | G06T 11/206 |
| | | | 345/440.1 |
| 2013/0274582 A1 * | 10/2013 | Afonso | A61B 5/066 |
| | | | 600/374 |
| 2015/0057507 A1 | 2/2015 | Koyrakh et al. | |
| 2015/0228254 A1 * | 8/2015 | Olson | G16H 50/50 |
| | | | 345/592 |
| 2016/0073913 A1 * | 3/2016 | Francis | A61B 5/339 |
| | | | 600/374 |

OTHER PUBLICATIONS

Lu, J. et al., "Contrast Enhancement of Medical Images Using Multiscale Edge Representation," Optical Engineering, Soc. of Photo-Optical Instrumentation Engineers, Bellingham, vol. 33, No. 7, Jul. 1, 1994.

* cited by examiner

US 11,380,029 B2

SYSTEM AND METHOD FOR MAPPING LOCAL ACTIVATION TIMES

CROSS-REFERENCE TO RELATED APPLICATIONS

This application claims the benefit of U.S. provisional application No. 62/507,289, filed 17 May 2017, which is hereby incorporated by reference as though fully set forth herein.

BACKGROUND

The present disclosure relates generally to cardiac therapeutic procedures, such as cardiac ablation. In particular, the present disclosure relates to systems, apparatuses, and methods for generating maps of local activation times.

Electrophysiological mapping, and more particularly electrocardiographic mapping, is a part of numerous cardiac and diagnostic and therapeutic procedures. As the complexity of such procedures increases, however, the electrophysiology maps utilized must increase in quality, in density, and in the rapidity and ease with which they can be generated.

Electrophysiology studies can include the creation of a local activation time ("LAT") map. LAT maps can, for example, provide insight to a practitioner as to how an arrhythmia is traveling throughout the cardiac chambers.

It can be challenging, however, to visualize certain arrhythmias, such as supraventricular and/or ventricular extrasystoles, using extant LAT maps.

BRIEF SUMMARY

Disclosed herein is a method of mapping local activation times from a plurality of electrophysiology data points, including the steps of: computing an LAT range for the plurality of electrophysiology data points; splitting the LAT range into at least a first LAT sub-range and a second LAT sub-range; defining at least a first subset of the plurality of electrophysiology data points falling within the first LAT sub-range and a second subset of the plurality of electrophysiology data points falling within the second LAT sub-range; and generating at least a first LAT sub-map of the first subset of the plurality of electrophysiology data points using a first mapping sub-convention and a second LAT sub-map of the second subset of the plurality of electrophysiology data points using a second mapping sub-convention.

In embodiments of the disclosure, the first mapping sub-convention is continuous with the second mapping sub-convention. For example, the first mapping sub-convention can include a first color spectrum and the second mapping sub-convention can include a second color spectrum that is continuous with the first color spectrum. As another example, the first mapping sub-convention can include a first grayscale range and the second mapping sub-convention can include a second grayscale range that is continuous with the first grayscale. As yet another example, the first mapping sub-convention can include a first pattern density range and the second mapping sub-convention can include a second pattern density range that is continuous with the first pattern density range.

The first and second mapping sub-conventions can be scaled to their respective LAT sub-ranges. For example, the first mapping sub-convention can be linearly scaled to the first LAT sub-range and the second mapping sub-convention can be linearly scaled to the second LAT sub-range. Alternatively, the first mapping sub-convention can be logarithmically scaled to the first LAT sub-range and the second mapping sub-convention can be logarithmically scaled to the second LAT sub-range.

According to aspects of the disclosure, the first LAT sub-range covers less than 50% of the LAT range and the second LAT sub-range covers more than 50% of the LAT range. For example, the first LAT sub-range can cover about 5% of the LAT range and the second LAT sub-range can cover about 95% of the LAT range.

The method can also include collecting an additional electrophysiology data point and then repeating, including the additional electrophysiology data point in the plurality of electrophysiology data points, the steps of: recomputing a LAT range for the plurality of electrophysiology data points; splitting the LAT range into at least a first LAT sub-range and a second LAT sub-range; and defining at least a first subset of the plurality of electrophysiology data points falling within the first LAT sub-range and a second subset of the plurality of electrophysiology data points falling within the second LAT sub-range; and generating at least a first LAT sub-map of the first subset of the plurality of electrophysiology data points using a first mapping sub-convention and a second LAT sub-map of the second subset of the plurality of electrophysiology data points using a second mapping sub-convention.

In additional aspects of the disclosure, the method can also include outputting a graphical representation of at least the first LAT sub-map and the second LAT sub-map on a three-dimensional cardiac model.

Also disclosed herein is a method of mapping local activation times, including: receiving an LAT map for at least a portion of a heart, wherein the LAT map is associated with a mapping convention; computing an LAT range for the LAT map; splitting the LAT range into a plurality of LAT sub-ranges; and splitting the LAT map into a plurality of LAT sub-maps, wherein a number of LAT sub-maps corresponds to a number of LAT sub-ranges, wherein each LAT sub-map of the plurality of LAT sub-maps is associated with a respective mapping sub-convention of a plurality of mapping sub-conventions.

The plurality of mapping sub-conventions can be continuous and can collectively comprise the mapping convention. For example, the mapping convention can include a color spectrum, a grayscale, and/or a pattern density range.

The method can also include outputting a graphical representation of the plurality of LAT sub-maps on a three-dimensional cardiac model.

According to aspects of the disclosure, the plurality of LAT sub-ranges includes a first LAT sub-range and a second LAT sub-range, wherein the first LAT sub-range is less than 50% of the LAT range (e.g., about 5% of the LAT range) and the second LAT sub-range is more than 50% of the LAT range (e.g., about 95% of the LAT range).

The instant disclosure also provides a system for mapping local activation times, including a mapping processor configured to: receive as input an LAT map for at least a portion of a heart, wherein the LAT map is associated with a mapping convention; compute an LAT range for the LAT map; split the LAT range into a plurality of LAT sub-ranges; and split the LAT map into a plurality of LAT sub-maps, wherein a number of LAT sub-maps corresponds to a number of LAT sub-ranges, wherein each LAT sub-map of the plurality of LAT sub-maps is associated with a respective mapping sub-convention of a plurality of mapping sub-conventions.

The system can also include an output processor configured to output a graphical representation of the plurality of LAT sub-maps on a three-dimensional cardiac model.

The foregoing and other aspects, features, details, utilities, and advantages of the present invention will be apparent from reading the following description and claims, and from reviewing the accompanying drawings.

While multiple embodiments are disclosed, still other embodiments of the present disclosure will become apparent to those skilled in the art from the following detailed description, which shows and describes illustrative embodiments. Accordingly, the drawings and detailed description are to be regarded as illustrative in nature and not restrictive.

DETAILED DESCRIPTION

The instant disclosure provides systems, apparatuses, and methods for generating maps of local activation time ("LAT"). For purposes of illustration, aspects of the disclosure will be described in connection with the mapping of extrasystoles. It should be understood, however, that the teachings herein can be applied to good advantage in other contexts (e.g., in the creation of other electrophysiology maps).

Figure 1:
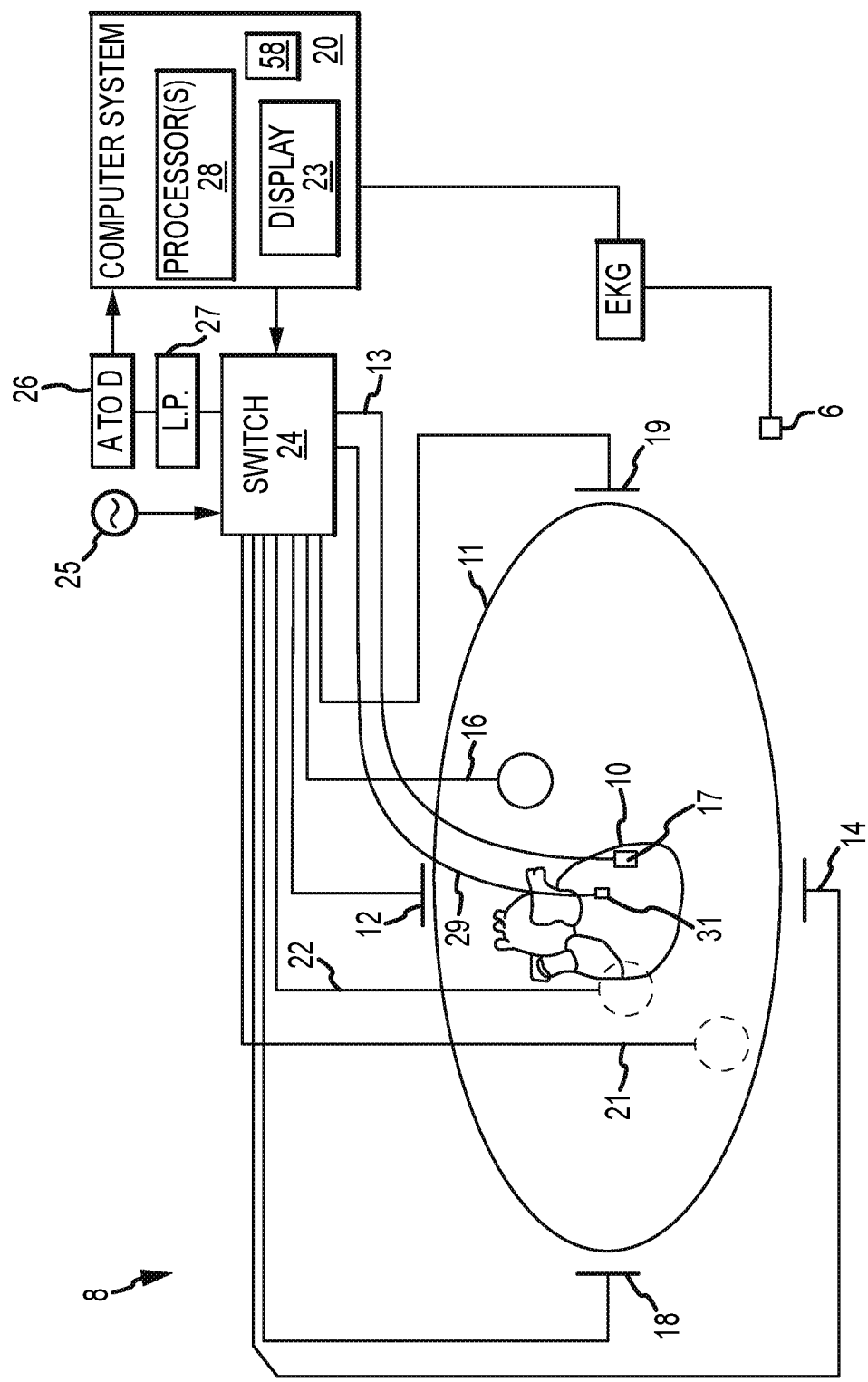
FIG. 1 is a schematic diagram of an exemplary electroanatomical mapping system.

FIG. 1 shows a schematic diagram of an exemplary electroanatomical mapping system 8 for conducting cardiac electrophysiology studies by navigating a cardiac catheter and measuring electrical activity occurring in a heart 10 of a patient 11 and three-dimensionally mapping the electrical activity and/or information related to or representative of the electrical activity so measured. System 8 can be used, for example, to create an anatomical model of the patient's heart 10 using one or more electrodes. System 8 can also be used to measure electrophysiology data at a plurality of points along a cardiac surface and store the measured data in association with location information for each measurement point at which the electrophysiology data was measured, for example to create a diagnostic data map of the patient's heart 10. In some embodiments, and as discussed further herein, the system 8 can generate LAT maps.

As one of ordinary skill in the art will recognize, and as will be further described below, system 8 determines the location, and in some aspects the orientation, of objects, typically within a three-dimensional space, and expresses those locations as position information determined relative to at least one reference.

For simplicity of illustration, the patient 11 is depicted schematically as an oval. In the embodiment shown in FIG. 1, three sets of surface electrodes (e.g., patch electrodes) are shown applied to a surface of the patient 11, defining three generally orthogonal axes, referred to herein as an x-axis, a y-axis, and a z-axis. In other embodiments the electrodes could be positioned in other arrangements, for example multiple electrodes on a particular body surface. As a further alternative, the electrodes do not need to be on the body surface, but could be positioned internally to the body.

In FIG. 1, the x-axis surface electrodes 12, 14 are applied to the patient along a first axis, such as on the lateral sides of the thorax region of the patient (e.g., applied to the patient's skin underneath each arm) and may be referred to as the Left and Right electrodes. The y-axis electrodes 18, 19 are applied to the patient along a second axis generally orthogonal to the x-axis, such as along the inner thigh and neck regions of the patient, and may be referred to as the Left Leg and Neck electrodes. The z-axis electrodes 16, 22 are applied along a third axis generally orthogonal to both the x-axis and the y-axis, such as along the sternum and spine of the patient in the thorax region, and may be referred to as the Chest and Back electrodes. The heart 10 lies between these pairs of surface electrodes 12/14, 18/19, and 16/22.

An additional surface reference electrode (e.g., a "belly patch") 21 provides a reference and/or ground electrode for the system 8. The belly patch electrode 21 may be an alternative to a fixed intra-cardiac electrode 31, described in further detail below. It should also be appreciated that, in addition, the patient 11 may have most or all of the conventional electrocardiogram ("ECG" or "EKG") system leads in place. In certain embodiments, for example, a standard set of 12 ECG leads may be utilized for sensing electrocardiograms on the patient's heart 10. This ECG information is available to the system 8 (e.g., it can be provided as input to computer system 20). Insofar as ECG leads are well understood, and for the sake of clarity in the figures, only a single lead 6 and its connection to computer 20 is illustrated in FIG. 1.

A representative catheter 13 having at least one electrode 17 is also shown. This representative catheter electrode 17 is referred to as the "roving electrode," "moving electrode," or "measurement electrode" throughout the specification. Typically, multiple electrodes 17 on catheter 13, or on multiple such catheters, will be used. In one embodiment, for example, the system 8 may comprise sixty-four electrodes on twelve catheters disposed within the heart and/or vasculature of the patient. Of course, this embodiment is merely exemplary, and any number of electrodes and catheters may be used.

Figure 2:
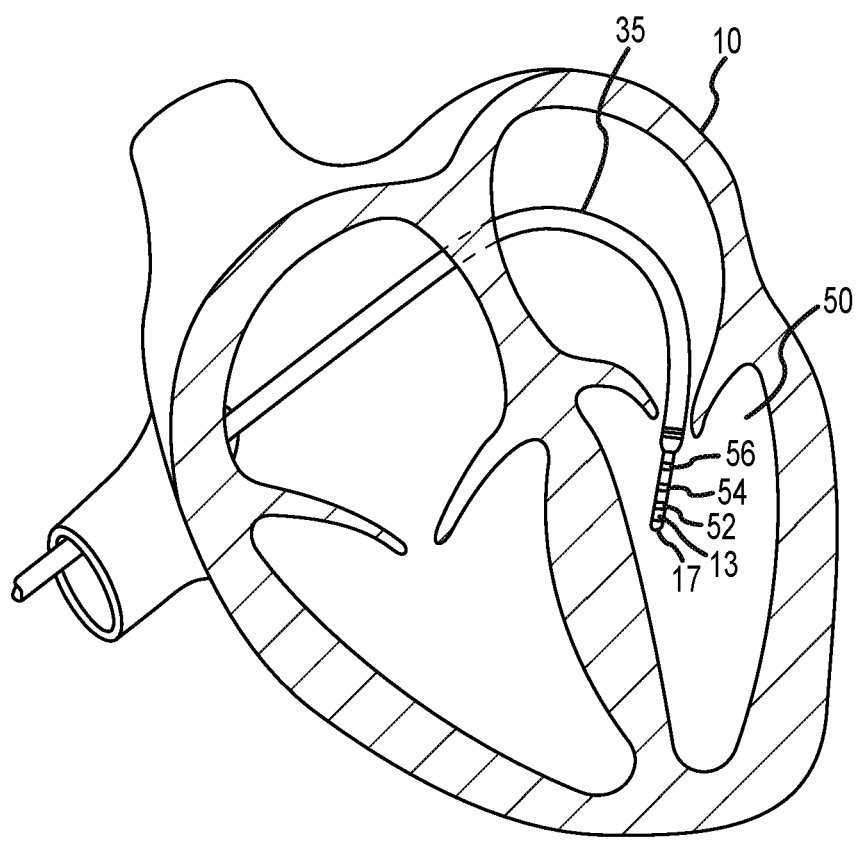
FIG. 2 depicts an exemplary catheter that can be used in connection with aspects of the instant disclosure.

Likewise, it should be understood that catheter 13 (or multiple such catheters) are typically introduced into the heart and/or vasculature of the patient via one or more introducers and using familiar procedures. For purposes of this disclosure, a segment of an exemplary multi-electrode catheter 13 is shown in FIG. 2. In FIG. 2, catheter 13 extends into the left ventricle 50 of the patient's heart 10 through a transseptal sheath 35. The use of a transseptal approach to the left ventricle is well known and will be familiar to those of ordinary skill in the art, and need not be further described herein. Of course, catheter 13 can also be introduced into the heart 10 in any other suitable manner.

Catheter 13 includes electrode 17 on its distal tip, as well as a plurality of additional measurement electrodes 52, 54, 56 spaced along its length in the illustrated embodiment. Typically, the spacing between adjacent electrodes will be known, though it should be understood that the electrodes may not be evenly spaced along catheter 13 or of equal size to each other. Since each of these electrodes 17, 52, 54, 56 lies within the patient, location data may be collected simultaneously for each of the electrodes by system 8.

Similarly, each of electrodes 17, 52, 54, and 56 can be used to gather electrophysiological data from the cardiac surface. The ordinarily skilled artisan will be familiar with various modalities for the acquisition and processing of electrophysiology data points (including, for example, both contact and non-contact electrophysiological mapping), such that further discussion thereof is not necessary to the understanding of the techniques disclosed herein. Likewise, various techniques familiar in the art can be used to generate a graphical representation from the plurality of electrophysiology data points. Insofar as the ordinarily skilled artisan will appreciate how to create electrophysiology maps from electrophysiology data points, the aspects thereof will only be described herein to the extent necessary to understand the instant disclosure.

Returning now to FIG. 1, in some embodiments, an optional fixed reference electrode 31 (e.g., attached to a wall of the heart 10) is shown on a second catheter 29. For calibration purposes, this electrode 31 may be stationary (e.g., attached to or near the wall of the heart) or disposed in a fixed spatial relationship with the roving electrodes (e.g., electrodes 17), and thus may be referred to as a "navigational reference" or "local reference." The fixed reference electrode 31 may be used in addition or alternatively to the surface reference electrode 21 described above. In many instances, a coronary sinus electrode or other fixed electrode in the heart 10 can be used as a reference for measuring voltages and displacements; that is, as described below, fixed reference electrode 31 may define the origin of a coordinate system.

Each surface electrode is coupled to a multiplex switch 24, and the pairs of surface electrodes are selected by software running on a computer 20, which couples the surface electrodes to a signal generator 25. Alternately, switch 24 may be eliminated and multiple (e.g., three) instances of signal generator 25 may be provided, one for each measurement axis (that is, each surface electrode pairing).

The computer 20 may comprise, for example, a conventional general-purpose computer, a special-purpose computer, a distributed computer, or any other type of computer. The computer 20 may comprise one or more processors 28, such as a single central processing unit ("CPU"), or a plurality of processing units, commonly referred to as a parallel processing environment, which may execute instructions to practice the various aspects described herein.

Generally, three nominally orthogonal electric fields are generated by a series of driven and sensed electric dipoles (e.g., surface electrode pairs 12/14, 18/19, and 16/22) in order to realize catheter navigation in a biological conductor. Alternatively, these orthogonal fields can be decomposed and any pairs of surface electrodes can be driven as dipoles to provide effective electrode triangulation. Likewise, the electrodes 12, 14, 18, 19, 16, and 22 (or any number of electrodes) could be positioned in any other effective arrangement for driving a current to or sensing a current from an electrode in the heart. For example, multiple electrodes could be placed on the back, sides, and/or belly of patient 11. Additionally, such non-orthogonal methodologies add to the flexibility of the system. For any desired axis, the potentials measured across the roving electrodes resulting from a predetermined set of drive (source-sink) configurations may be combined algebraically to yield the same effective potential as would be obtained by simply driving a uniform current along the orthogonal axes.

Thus, any two of the surface electrodes 12, 14, 16, 18, 19, 22 may be selected as a dipole source and drain with respect to a ground reference, such as belly patch 21, while the unexcited electrodes measure voltage with respect to the ground reference. The roving electrodes 17 placed in the heart 10 are exposed to the field from a current pulse and are measured with respect to ground, such as belly patch 21. In practice the catheters within the heart 10 may contain more or fewer electrodes than the sixteen shown, and each electrode potential may be measured. As previously noted, at least one electrode may be fixed to the interior surface of the heart to form a fixed reference electrode 31, which is also measured with respect to ground, such as belly patch 21, and which may be defined as the origin of the coordinate system relative to which system 8 measures positions. Data sets from each of the surface electrodes, the internal electrodes, and the virtual electrodes may all be used to determine the location of the roving electrodes 17 within heart 10.

The measured voltages may be used by system 8 to determine the location in three-dimensional space of the electrodes inside the heart, such as roving electrodes 17 relative to a reference location, such as reference electrode 31. That is, the voltages measured at reference electrode 31 may be used to define the origin of a coordinate system, while the voltages measured at roving electrodes 17 may be used to express the location of roving electrodes 17 relative to the origin. In some embodiments, the coordinate system is a three-dimensional (x, y, z) Cartesian coordinate system, although other coordinate systems, such as polar, spherical, and cylindrical coordinate systems, are contemplated.

As should be clear from the foregoing discussion, the data used to determine the location of the electrode(s) within the heart is measured while the surface electrode pairs impress an electric field on the heart. The electrode data may also be used to create a respiration compensation value used to improve the raw location data for the electrode locations as described, for example, in U.S. Pat. No. 7,263,397, which is hereby incorporated herein by reference in its entirety. The electrode data may also be used to compensate for changes in the impedance of the body of the patient as described, for example, in U.S. Pat. No. 7,885,707, which is also incorporated herein by reference in its entirety.

Therefore, in one representative embodiment, system 8 first selects a set of surface electrodes and then drives them with current pulses. While the current pulses are being delivered, electrical activity, such as the voltages measured with at least one of the remaining surface electrodes and in vivo electrodes, is measured and stored. Compensation for artifacts, such as respiration and/or impedance shifting, may be performed as indicated above.

In some embodiments, system 8 is the EnSite™ Velocity™ or EnSite Precision™ cardiac mapping and visualization system of Abbott Laboratories. Other localization systems, however, may be used in connection with the present teachings, including for example the CARTO navigation and location system of Biosense Webster, Inc., the AURORA® system of Northern Digital Inc., Sterotaxis' NIOBE® Magnetic Navigation System, as well as MediGuide™ Technology from Abbott Laboratories.

The localization and mapping systems described in the following patents (all of which are hereby incorporated by reference in their entireties) can also be used with the present invention: U.S. Pat. Nos. 6,990,370; 6,978,168; 6,947,785; 6,939,309; 6,728,562; 6,640,119; 5,983,126; and 5,697,377.

Aspects of the disclosure relate to generating LAT maps. System 8 can therefore also include a LAT mapping module 58 that can be used to generate LAT maps.

A LAT map is a type of electrophysiology map. Those of ordinary skill in the art will appreciate that electrophysiology maps, including, but not limited to, LAT maps, include a plurality of electrophysiology data points, and that each electrophysiology data point in turn includes both measured electrophysiology data (e.g., an electrophysiological signal, such as a cardiac electrogram ("EGM")) and location data (e.g., information regarding the location of catheter 13 and/or electrodes 17, 52, 54, 56 thereon), allowing the measured electrophysiology information to be associated with a particular location in space (that is, allowing the measured electrophysiology information to be interpreted as indicative of electrical activity at a point on the patient's heart).

Those of ordinary skill in the art will also be familiar with various aspects of the collection of electrophysiology data points and the creation of electrophysiology maps therefrom. By way of example only, however, United States patent application publication no. 2015/0057507, which is hereby incorporated by reference as though fully set forth herein, describes various methods and systems for the collection of electrophysiology data points and the creation of electrophysiology maps to which the teachings of the instant disclosure can be applied.

Figure 3:
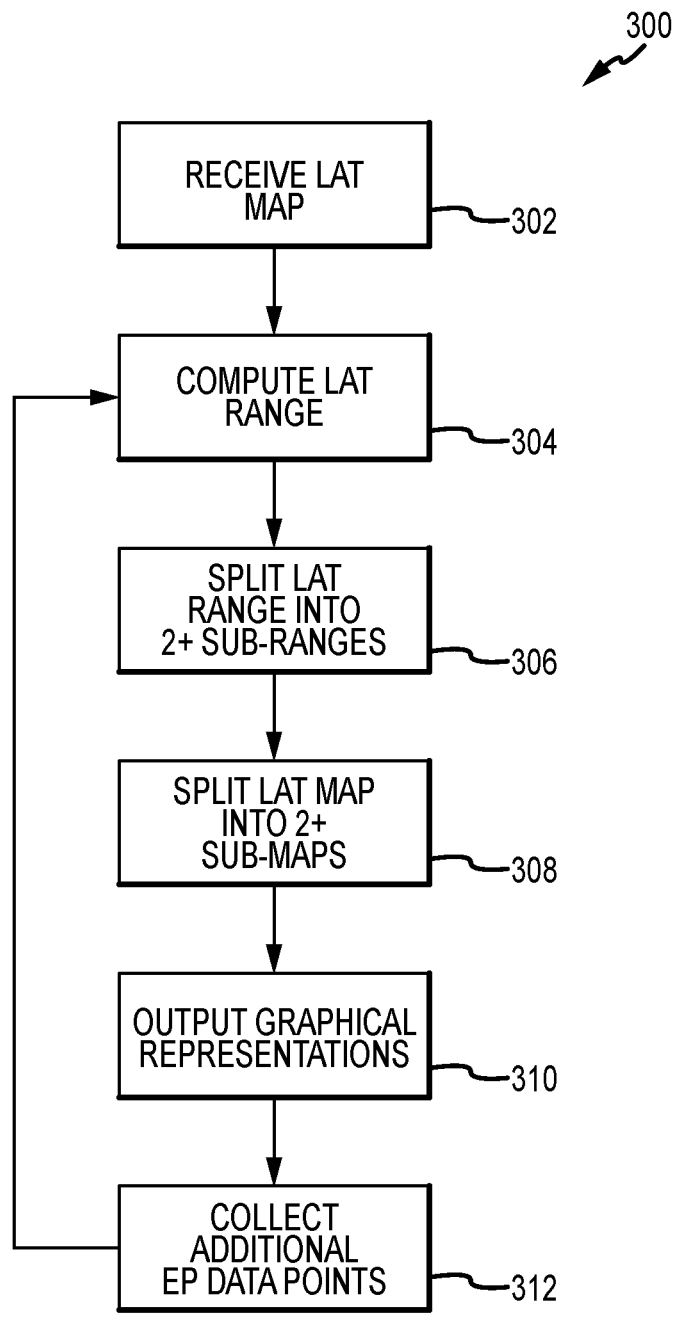
FIG. 3 is a flowchart of representative steps that can be followed according to exemplary embodiments disclosed herein.

One exemplary method of mapping LATs, such as from a plurality of electrophysiology data points, according to the present teachings will be explained with reference to the flowchart 300 of representative steps presented as FIG. 3. In some embodiments, for example, flowchart 300 may represent several exemplary steps that can be carried out by electroanatomical mapping system 8 of FIG. 1 (e.g., by processor 28 and/or LAT mapping module 58). It should be understood that the representative steps described below can be either hardware- or software-implemented. For the sake of explanation, the term "signal processor" is used herein to describe both hardware- and software-based implementations of the teachings herein.

A LAT map for at least a portion of a heart is received in block 302. Those of ordinary skill in the art will appreciate that the LAT map received in block 302 includes a plurality of electrophysiology data points, each having an associated LAT (in addition to other location and electrophysiological information).

Those of ordinary skill in the art will also recognize that the LAT map can be associated with a mapping convention, such as a color spectrum, a grayscale, a pattern density range, or the like. This mapping convention can be applied to the LAT map data when rendering a graphical representation of the LAT map, for example on a three-dimensional cardiac model. Insofar as those of ordinary skill in the art will be generally familiar with the graphical representation of electrophysiology maps, including LAT maps, further details of the same are not necessary to an understanding of the instant disclosure.

In block 304, an LAT range is computed. The LAT range is the variation between the earliest and latest LATs within the LAT map.

In block 306, the LAT range is split into a plurality of LAT sub-ranges. According to aspects of the disclosure, the LAT range is split into a first LAT sub-range that covers less than 50% of the LAT range and a second LAT sub-range that covers the remainder of the LAT range. For example, in embodiments disclosed herein, the first LAT sub-range covers the earliest 5% of the LAT range, while the second LAT sub-range covers the remaining 95% of the LAT range. In other words, according to aspects of the disclosure, the LAT sub-ranges collectively constitute the LAT range. It is also contemplated, however, that the LAT sub-ranges collectively constitute less than the entire LAT range (e.g., if there is a portion of the LAT range that is not of interest to the practitioner, that portion of the LAT range need not be reflected in a LAT sub-range). As discussed below, by splitting the LAT range into sub-ranges, increased granularity can be achieved when graphically representing some LAT sub-maps relative to other LAT sub-maps.

In block 308, the LAT map is split into a plurality of LAT sub-maps. In general, the number of LAT sub-maps will correspond to the number of LAT sub-ranges (e.g., for two LAT sub-ranges, there will be two LAT sub-maps, one corresponding to each LAT sub-range).

Thus, for example, a first LAT sub-map can be generated by identifying a first subset of the plurality of electrophysiology data points in the LAT map that have LATs falling within the first LAT sub-range. Similarly, a second LAT sub-map can be generated by identifying a second subset of the plurality of electrophysiology data points in the LAT map that have LATs falling within the second LAT sub-range.

Each of the LAT sub-maps will also have an associated mapping sub-convention. It is desirable for the mapping sub-conventions to be continuous and to collectively cover the mapping convention for the LAT map.

According to some aspects of the disclosure, the mapping sub-conventions are linearly scaled to their respective LAT sub-ranges. In other aspects of the disclosure, the mapping sub-conventions are logarithmically scaled to their respective LAT sub-ranges. Of course, the mapping sub-conventions can be scaled to their respective LAT sub-ranges in other ways without departing from the scope of the present teachings. Moreover, combinations of scales are contemplated (e.g., one mapping sub-convention can be linearly scaled to its respective LAT sub-range, while another mapping sub-convention can be logarithmically scaled to its respective LAT sub-range).

For example, if the mapping convention is a color spectrum (e.g., white to purple), the first LAT sub-map can have a first mapping sub-convention that is a first color spectrum (e.g., white to orange) that is linearly scaled to the first LAT sub-range, and the second LAT sub-map can have a second mapping sub-convention that is a second color spectrum (e.g., yellow to purple) that is linearly scaled to the second LAT sub-range.

As another example, if the mapping convention is a grayscale, the first LAT sub-map can have a first mapping sub-convention that is a first grayscale range that is linearly scaled to the first LAT sub-range, and the second LAT sub-map can have a second mapping sub-convention that is a second grayscale range that is linearly scaled to the second LAT sub-range.

Likewise, if the mapping convention is a pattern density range, then the first LAT sub-map can have a first mapping sub-convention that covers a first portion of the total pattern density range and that is linearly scaled to the first LAT sub-range, and the second LAT sub-map can have a second mapping sub-convention that covers the remainder of the total pattern density range and that is linearly scaled to the second LAT sub-range.

In other embodiments, the mapping sub-conventions are discontinuous. For example, the first mapping sub-convention can be a color spectrum, while the second mapping convention can be a grayscale range.

Figure 4:
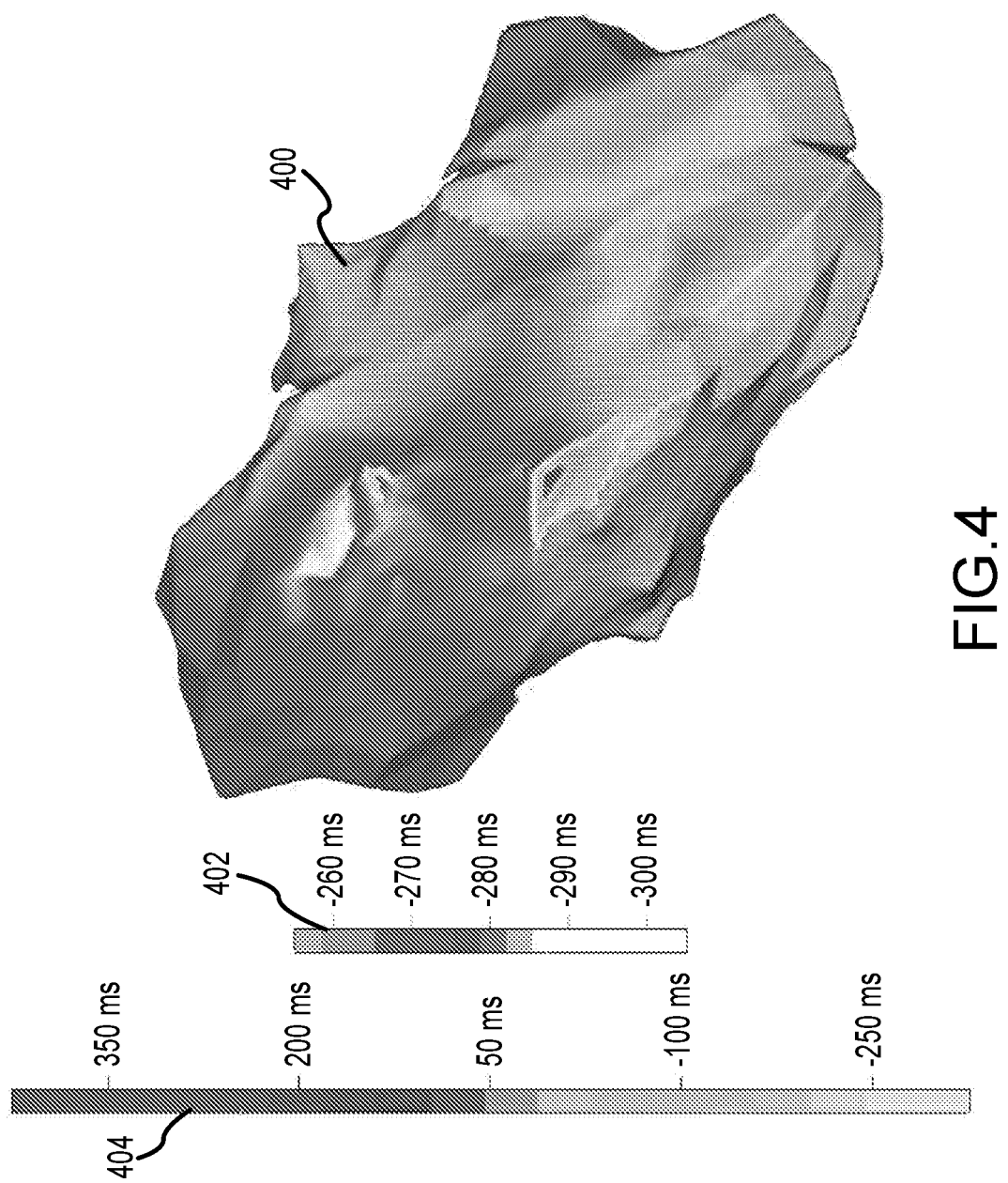
FIG. 4 is a representative LAT map according to the teachings herein.

Graphical representations of the LAT sub-maps can be output in block 310. For example, FIG. 4 is an illustrative graphical representation 400 generated according to the foregoing disclosure (e.g., generated by LAT module 58 and output on display 23 of FIG. 1). As shown in FIG. 4, graphical representation 400 utilizes a first mapping sub-convention (e.g., grayscale range) 402 to depict the earliest 5% of LATs (e.g., about −300 ms to about −260 ms) and a second mapping sub-convention (e.g., grayscale range) 404 to depict the remaining 95% of LATs (e.g., about −250 ms to about 350 ms).

Additional electrophysiology data points can be added beginning in block 312. After one (or more) additional electrophysiology data points are collected in block 312, the process can return to block 304 to recompute the LAT range, resplit the LAT range, and regenerate the LAT sub-maps to include the newly collected electrophysiology data point(s).

The instant teachings can be applied to good advantage when mapping extrasystoles. Specifically, the instant teachings allow for improved visualization of the location of earliest activation by using a dedicated mapping sub-convention for the earliest 5% of LATs (as opposed to including all LATs in a single mapping convention). As but one example of this improved visualization, the instant teachings allow for a mapping convention that is overall non-linear, but that is made up of a plurality of linear mapping sub-conventions, thereby improving visualization of a portion (or portions) of the overall LAT range by allowing for increased graphical granularity of one or more LAT sub-ranges of particular interest to the practitioner.

Although several embodiments have been described above with a certain degree of particularity, those skilled in the art could make numerous alterations to the disclosed embodiments without departing from the spirit or scope of this invention.

For example, the teachings herein could be extended to greater than two sub-ranges of the LAT range.

As another example, the teachings herein can be applied in real time (e.g., during an electrophysiology study) or during post-processing (e.g., to electrophysiology data points collected during an electrophysiology study performed at an earlier time).

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A method of mapping local activation times from a plurality of electrophysiology data points, the method comprising:
    computing an LAT range for the plurality of electrophysiology data points;
    splitting the LAT range into at least a first LAT sub-range and a second LAT sub-range;
    defining at least a first subset of the plurality of electrophysiology data points falling within the first LAT sub-range and a second subset of the plurality of electrophysiology data points falling within the second LAT sub-range; and
    generating at least a first LAT sub-map of the first subset of the plurality of electrophysiology data points using a first mapping sub-convention and a second LAT sub-map of the second subset of the plurality of electrophysiology data points using a second mapping sub-convention,
    wherein the first mapping sub-convention is continuous with the second mapping sub-convention,
    the first mapping sub-convention is scaled to the first LAT sub-range,
    the second mapping sub-convention is scaled to the second LAT sub-range, and
    the scale of the first mapping sub-convention to the first LAT sub-range differs from the scale of the second mapping sub-convention to the second LAT sub-range.

2. The method according to claim 1, wherein the first mapping sub-convention comprises a first color spectrum and the second mapping sub-convention comprises a second color spectrum.

3. The method according to claim 1, wherein the first mapping sub-convention comprises a first grayscale range and the second mapping sub-convention comprises a second grayscale range.

4. The method according to claim 1, wherein the first mapping sub-convention comprises a first pattern density range and the second mapping sub-convention comprises a second pattern density range.

5. The method according to claim 1, wherein the first mapping sub-convention is linearly scaled to the first LAT sub-range and the second mapping sub-convention is linearly scaled to the second LAT sub-range, and wherein a slope of the linear scale of the first mapping convention to the first LAT sub-range differs from a slope of the linear scale of the second mapping convention to the second LAT sub-range.

6. The method according to claim 1, wherein the first mapping sub-convention is logarithmically scaled to the first LAT sub-range and the second mapping sub-convention is logarithmically scaled to the second LAT sub-range.

7. The method according to claim 6, wherein the first LAT sub-range covers 5% of the LAT range and the second LAT sub-range covers 95% of the LAT range.

8. The method according to claim 1, wherein the first LAT sub-range covers less than 50% of the LAT range and the second LAT sub-range covers more than 50% of the LAT range.

9. The method according to claim 1, further comprising:
    collecting an additional electrophysiology data point; and
    repeating, including the additional electrophysiology data point in the plurality of electrophysiology data points, the steps of:
        recomputing a LAT range for the plurality of electrophysiology data points;
        splitting the LAT range into at least a first LAT sub-range and a second LAT sub-range; and
        defining at least a first subset of the plurality of electrophysiology data points falling within the first LAT sub-range and a second subset of the plurality of electrophysiology data points falling within the second LAT sub-range; and
        generating at least a first LAT sub-map of the first subset of the plurality of electrophysiology data points using a first mapping sub-convention and a second LAT sub-map of the second subset of the plurality of electrophysiology data points using a second mapping sub-convention.

10. The method according to claim 1, further comprising outputting a graphical representation of at least the first LAT sub-map and the second LAT sub-map on a three-dimensional cardiac model.

11. A method of mapping local activation times, comprising:
    receiving an LAT map for at least a portion of a heart, wherein the LAT map is associated with a mapping convention;
    computing an LAT range for the LAT map;
    splitting the LAT range into a plurality of LAT sub-ranges; and
    splitting the LAT map into a plurality of LAT sub-maps, wherein a number of LAT sub-maps corresponds to a number of LAT sub-ranges,
    wherein each LAT sub-map of the plurality of LAT sub-maps is associated with a respective mapping sub-convention of a plurality of mapping sub-conventions,
    wherein the plurality of mapping sub-conventions are continuous and collectively comprise the mapping convention,
    wherein each mapping sub-convention of the plurality of mapping sub-conventions is scaled to a respective LAT sub-map of the plurality of LAT sub-maps, and
    wherein a first scale of a first mapping sub-convention of the plurality of mapping sub-conventions to a respective first LAT sub-map differs from a second scale of a second mapping sub-convention of the plurality of mapping sub-conventions to a respective second LAT sub-map.

12. The method according to claim 11, wherein the mapping convention comprises a color spectrum.

13. The method according to claim 11, wherein the mapping convention comprises a grayscale.

14. The method according to claim 11, wherein the mapping convention comprises a pattern density range.

15. The method according to claim 10, further comprising outputting a graphical representation of the plurality of LAT sub-maps on a three-dimensional cardiac model.

16. The method according to claim 15, wherein the first LAT sub-range is 5% of the LAT range and the second LAT sub-range is 95% of the LAT range.

17. The method according to claim 11, wherein the first LAT sub-range is less than 50% of the LAT range and the second LAT sub-range is more than 50% of the LAT range.

18. A system for mapping local activation times, comprising:
    a mapping processor configured to:
        receive as input an LAT map for at least a portion of a heart, wherein the LAT map is associated with a mapping convention;
        compute an LAT range for the LAT map;
        split the LAT range into a plurality of LAT sub-ranges; and
        split the LAT map into a plurality of LAT sub-maps, wherein a number of LAT sub-maps corresponds to a number of LAT sub-ranges, wherein each LAT sub-map of the plurality of LAT sub-maps is associated with a respective mapping sub-convention of a plurality of mapping sub-conventions,
    wherein a scale of a first mapping sub-convention of the plurality of mapping sub-conventions to a respective first LAT sub-map of the plurality of LAT sub-maps differs from a scale of a second mapping sub-convention of the plurality of mapping sub-conventions to a respective second LAT sub-map of the plurality of LAT sub-maps.

19. The system according to claim 18, further comprising an output processor configured to output a graphical representation of the plurality of LAT sub-maps on a three-dimensional cardiac model.

* * * * *